US00PP18692P3

(12) United States Plant Patent
Sanders

(10) Patent No.: US PP18,692 P3
(45) Date of Patent: Apr. 1, 2008

(54) **NEW GUINEA *IMPATIENS* PLANT NAMED 'INGCARROSB'**

(50) Latin Name: *Impatiens hawkeri*
Varietal Denomination: Ingcarrosb

(75) Inventor: Monica Maria Adelheid Sanders, Grootebroek (NL)

(73) Assignee: Syngenta Seed B.V., Enkhuizen (NL)

( * ) Notice: Subject to any disclaimer, the term of this patent is extended or adjusted under 35 U.S.C. 154(b) by 0 days.

(21) Appl. No.: 11/447,317

(22) Filed: Jun. 6, 2006

(65) Prior Publication Data

US 2007/0283471 P1 Dec. 6, 2007

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
*Assistant Examiner*—Louanne Krawczewicz Myers
(74) *Attorney, Agent, or Firm*—Bruce Vrana

(57) ABSTRACT

A new and distinct cultivar of New Guinea *Impatiens* plant named 'Ingcarrosb' characterized by its good branching habit with short internodes, medium sized dark green foliage, large dark rose flowers, and good vigor.

1 Drawing Sheet

Latin name of the genus and species of the plant claimed: *Impatiens hawkeri.*

Varietal denomination: 'Ingcarrosb'.

BACKGROUND OF THE NEW PLANT

The present invention comprises a new and distinct New Guinea *Impatiens* plant botanically known as *Impatiens hawkeri* and referred to by the cultivar name 'Ingcarrosb.'

The new cultivar was developed in a controlled breeding program conducted by the inventor in Enkhuizen, Netherlands. The New Guinea *Impatiens* cultivar is medium sized with an early flowering response, large flowers with attractive coloration and a good flowering behavior under field conditions.

The new cultivar is propagated from cuttings resulting from the cross in September 2002 of the proprietary New Guinea *Impatiens* selection identified as 'MM 199-1' as female parent and the proprietary New Guinea *Impatiens* selection identified as 'I 213-1' as male parent. 'MM 199-1' is not commercially available and has not been patented. 'I 213-1' is not commercially available and has not been patented.

As a result of this cross the present cultivar was selected in September 2003 in Enkhuizen, Netherlands and has been repeatedly asexually reproduced by cuttings in Enkhuizen, Netherlands, in Gilroy, Calif. and in Angers, France over a period of two years. The distinctive characteristics of this new *Impatiens* are stable and reproduced true to type in successive generations of asexual reproduction. It takes 8 to 10 weeks to produce a finished plant, starting from a rooted plug and planted in a 12 cm pot, depending on the temperature.

SUMMARY OF THE INVENTION

The following traits have been repeatedly observed and are determined to be the unique characteristics of 'Ingcarrosb'. These characteristics in combination distinguish 'Ingcarrosb' as a new and distinct New Guinea *Impatiens* cultivar:

1. Large dark rose flowers with a stable color.
2. Ball shaped plant habit with flowers on top of the foliage.
3. Dark green foliage.
4. Good basal branching character with short internodes.
5. Good outdoor vigor.

Plants of the New Guinea *Impatiens* named 'Ingcarrosb' differ primarily from the plants of the female parent selection in the following characteristic:

Plants of the New Guinea *Impatiens* named 'Ingcarrosb' have large dark rose flowers, whereas the plants of the female parent selection have medium purple flowers.

Plants of the new Guinea *Impatiens* named 'Ingcarrosb' differ primarily from the plants of the male parent selection in the following characteristic:

Plants of the New Guinea *Impatiens* named 'Ingcarrosb' have large dark rose flowers, whereas the plants of the male parent selection have medium purple flowers.

Plants of the New Guinea *Impatiens* name 'Ingcarrosb' can be compared to plants of 'Fisnics Purple,' U.S. Pat. No. 14,728. In side-by-side comparisons conducted in Enkhuizen, Netherlands, plants of the New Guinea *Impatiens* named 'Ingcarrosb' differed from plants of the cultivar 'Fisnics Purple' in the following characteristics:

1. Plants of the New Guinea *Impatiens* named 'Ingcarrosb' have short internodes and short flower stems, whereas the cultivar 'Fisnics Purple' has longer internodes and longer flower stems.
2. Plants of the New Guinea *Impatiens* named 'Ingcarrosb' have dark rose flowers, whereas the cultivar 'Fisnics Purple' has purple violet flowers.

DESCRIPTION OF THE DRAWING

The New Guinea *Impatiens* named 'Ingcarrosb' plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of the New Guinea *Impatiens* named 'Ingcarrosb'. The data which defines these characteristics were collected from asexual reproductions carried out in Enkhuizen, Netherlands. The plant history was taken on 30 week old plants, blossomed under natural light in the field.

Color readings were taken in the laboratory under ambient light. Color references are primarily to the RHS Colour Chart of the Royal Horticultural Society of London.

The plant:
- *Classification.*—Botanical: *Impatiens hawkeri.*

Parentage:
- *Female parent.*—Proprietary *Impatiens hawkeri* selection identified as code number 'MM 199-1,' not patented.
- *Male parent.*—Proprietary *Impatiens hawkeri* selection identified as code number 'I 213-1,' not patented.

Propagation:
- *Type cutting.*—Terminal cuttings.
- *Time to initiate roots.*—Approximately 7–14 days.
- *Time to produce a rooted cutting.*—Approximately 21 days.
- *Root description.*—Fine, fibrous, and white in color.

Plant description:
- *General appearance.*—Outwardly spreading, low rounded and uniform mounded plant growth.

Habit:
- *Growth and branching habit.*—Freely branching habit, freely flowering, moderate vigorous.

Crop time:
- *Plant height.*—28 cm.
- *Plant spread.*—40 cm.

Lateral branch description:
- *Number of lateral branches per plant.*—16–18.
- *Length.*—14–17 cm.
- *Diameter.*—4–7 mm.
- *Texture.*—Smooth, glabrous.
- *Internode length.*—0.7–5.5 cm.
- *Color.*—RHS 187A.

Foliage description:
- *Arrangement.*—Opposite in whorls.
- *Length, mature leaves.*—7.7 cm.
- *Width, mature leaves.*—2.3 cm.
- *Shape.*—Lanceolate.
- *Apex.*—Acuminate.
- *Base.*—Acute.
- *Margin.*—Serrulate with fine cilation.
- *Texture, upper surface.*—Smooth, slightly rugose.
- *Texture, lower surface.*—Smooth, glabrous.
- *Venation pattern.*—Pinnate.
- *Color young foliage, upper surface.*—RHS 147A.
- *Color young foliage, lower surface.*—RHS 187A.
- *Fully expanded foliage, upper surface.*—RHS 147A.
- *Fully expanded foliage, lower surface.*—RHS 187A.
- *Venation, upper surface.*—RHS 187B.
- *Venation, lower surface.*—RHS 187A.
- *Anthocyanin may be present.*—RHS 187A.
- *Petiole length.*—About 0.9 cm.
- *Petiole diameter.*—About 3.0 mm.
- *Texture of petiole.*—Smooth, glabrous.
- *Color of petiole.*—RHS 187C.

Flower description:
- *Flower type and flowering habit.*—Single.
- *Number of flowers per leaf axil.*—1.
- *Number of flowers and flower buds per lateral branch.*—5.
- *Flower position.*—Above and beyond the foliage and typically facing upwards and outward.
- *Flower shape.*—Rounded, mostly flat.
- *Flowers lasting.*—About 10 days on the plant depending on environmental conditions.
- *Petals.*—Self cleaning.
- *Gynoecium.*—Persistent.
- *Flowers.*—Not fragrant.
- *Flowering.*—Indeterminate and continuous.
- *Flowering season.*—Year round under greenhouse conditions. In the garden, flowering from spring until fall.
- *Flower length.*—About 6.7 cm.
- *Flower width.*—About 6.5 cm.
- *Flower depth.*—About 0.8 cm.

Flower buds:
- *Rate from opening.*—From flower bud to fully open flower, typically about 10 days, depending on temperature.
- *Bud length.*—About 2.6 cm.
- *Bud diameter.*—About 1.2 cm.
- *Bud shape.*—Ellipsoidal.
- *Texture.*—Smooth, glabrous.
- *Color, just before opening.*—RHS 58A.

Petals:
- *Quantity.*—Single, five per flower, imbricate.
- *Length of banner petal.*—About 3.2 cm.
- *Width of banner petal.*—About 4.6 cm.
- *Length lateral and basal petals.*—About 3.7 cm.
- *Width lateral and basal petals.*—About 3.5 cm.
- *Lateral and basal petal shape.*—Obcordate.
- *Banner petal shape.*—Obcordate.
- *Petal apex.*—Retuse to emarginate.
- *Petal base.*—Attenuate.
- *Petal margin.*—Entire.
- *Petal texture, upper surface.*—Smooth, satiny.
- *Petal texture, lower surface.*—Smooth.
- *Petal color.*—Upper surface: When opening and fully opened: RHS N66A. Lower surface: When opening and fully opened: RHS 58A.

Petal color — Small spot at base of all petals. —RHS N66C.

Sepals (lateral sepals):
- *Number of lateral sepals.*—2.
- *Length.*—11–13 mm.
- *Width.*—6–8 mm.
- *Shape.*—Ovate.
- *Apex.*—Caudate.
- *Base.*—Truncate.
- *Margin.*—Entire.
- *Color, upper side.*—RHS 63A.
- *Color, lower side* (*lower part of sepal*).—RHS N66A.
- *Color, lower side* (*near tip of sepal*).—RHS 139C.

Spur:
- *Number of spurs.*—One.
- *Length.*—About 4.5 cm.
- *Diameter of spur at apex.*—About 1 mm.
- *Diameter of spur at flower.*—About 3 mm.
- *Texture.*—Smooth, glabrous.

*Aspect.*—Curved.
*Color.*—RHS 53A.

Peduncles:
*Length.*—About 4 cm.
*Strength.*—Strong, flexible.
*Diameter.*—0.2 cm.
*Aspect.*—About 45° from the stem.
*Color.*—RHS 46A.

Reproductive organs:
*Androecium.*—Stamen number: Five fused at anthers, filaments free, hooded.
*Anther shape.*—Obovate.
*Anther length.*—About 5 mm.
*Anther color.*—RHS 53B to 16D, base to apex.
*Amount of pollen.*—Moderate.
*Pollen color.*—RHS 4D.

Gynoecium:
*Pistil number.*—One.
*Pistil length.*—About 3 mm.
*Stigma shape.*—Columnar, five segmented.
*Stigma color.*—RHS 60C.
*Style color.*—RHS 53A.
*Ovary arrangement.*—Five celled.
*Ovary color.*—RHS 144A.

Seed development: Seed development has not been observed.

Disease and pest resistance: Resistance to pathogens and pests common to *Impatiens* has not been observed.

What is claimed is:

1. A new and distinct cultivar of New Guinea *Impatiens* plant named 'Ingcarrosb', as substantially illustrated and described herein.

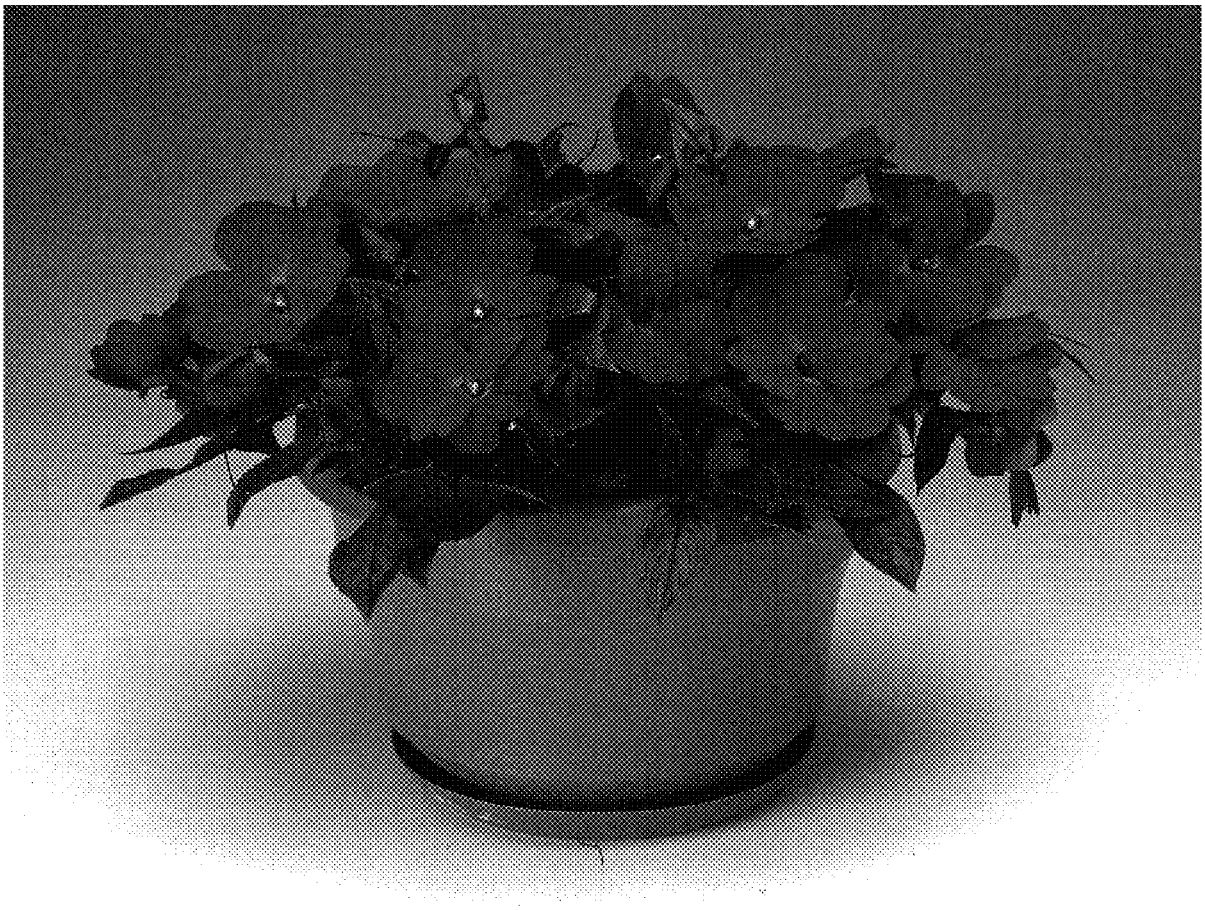

* * * * *